(12) United States Patent
Nieboer et al.

(10) Patent No.: US 6,995,003 B1
(45) Date of Patent: Feb. 7, 2006

(54) METHOD TO LOCALIZE EXPANDASE IN THE CYTOSOL

(75) Inventors: Maarten Nieboer, Delfgauw (NL); Roelof Ary Lans Bovenberg, Rotterdam (NL)

(73) Assignee: DSM IP Assets B.V., Te Heerlen (NL)

( * ) Notice: Subject to any disclaimer, the term of this patent is extended or adjusted under 35 U.S.C. 154(b) by 0 days.

(21) Appl. No.: 09/700,080

(22) PCT Filed: May 19, 1999

(86) PCT No.: PCT/EP99/03455

§ 371 (c)(1),
(2), (4) Date: Dec. 1, 2000

(87) PCT Pub. No.: WO99/60102

PCT Pub. Date: Nov. 25, 1999

(30) Foreign Application Priority Data

May 19, 1998 (EP) .................................. 98201655

(51) Int. Cl.
*C12N 9/04* (2006.01)
(52) U.S. Cl. .................... 435/190; 435/6; 435/252.3; 435/254.11; 435/419; 435/325; 536/23.2; 536/23.7
(58) Field of Classification Search .............. 536/23.1, 536/23.2; 435/320.1, 252.3
See application file for complete search history.

(56) References Cited

U.S. PATENT DOCUMENTS 4,003,894 A    1/1977    Verweij et al. ............. 260/243

FOREIGN PATENT DOCUMENTS

| EP | 0341892 | 11/1989 |
|---|---|---|
| EP | 0448180 | 9/1991 |
| EP | 0366354 B1 | 1/1996 |
| EP | 0532341 B1 | 11/1998 |
| WO | WO/9504148 A1 | 2/1995 |
| WO | WO/9504149 | 2/1995 |
| WO | WO/9720053 | 6/1997 |
| WO | WO/9802551 A2 | 1/1998 |

OTHER PUBLICATIONS

Theilgaard et al. (1987). "Purification and characterization of δ-(L-α-aminoadipyl)-L-cysteinyl-D-valine synthetase from *Penicillium chrysogenum*" *Biochem.J*. 327: 185-191.
Aharonowitz, et al. (1992). *Annu. Rev. Microbiol.* 46:461-495.
Coque et al. (1993). *Molecular General Genetics*. 236:453-458.
Cortés et al. (1987). *J. General Microbiology*. 113:3165-3174.
De Hoop, M.J. and AB G. (1992). *Biochem. J*. 286:657-669.
Gould, S.J., et al. (1989). *Journal of Cell Biology*. 108 (5):1657-1664.
Ingolia and Queener. (1989). *Medicinal Research Reviews*. 9(2):245-264.
Queener, S. W. et al. (1994). *Annals of the New York Academy of Sciences*. 721:178-193.

*Primary Examiner*—Kathleen Kerr
(74) *Attorney, Agent, or Firm*—Morrison & Foerster LLP

(57) ABSTRACT

The invention provides DNA, heterologous host cells capable of transcribing, translating or expressing said DNA and methods employing such host cells and cultures thereof for an improved in vivo production of acylated cephalosporins with higher yield. According to the invention, a host cell is provided comprising an enzyme having expandase activity which is predominantly localized in the cytosol (as opposed to localized mainly in or with the peroxisomes or microbodies) of the host cell.

14 Claims, 4 Drawing Sheets

A  B

METHOD TO LOCALIZE EXPANDASE IN THE CYTOSOL

This Application is the national phase of PCT/EP 99/03455 filed 19 May 1999 which claims priority from European application 98/201655.2 filed 19 May 1998.

FIELD OF THE INVENTION

The present invention lies in the field of recombinant DNA techniques. More in particular, the invention is in the field of the production of cephalosporins using genetically modified host organisms, host organisms so modified, as well as DNA for use therein. The invention further pertains to modified enzymes expressed from recombinant DNA in said host organisms.

BACKGROUND OF THE INVENTION

β-Lactam antibiotics constitute the most important group of antibiotic compounds, with a long history of clinical use. Among this group, the prominent ones are the penicillins and cephalosporins. These compounds are naturally produced by the filamentous fungi such as *Penicillium chrysogenum* and *Acremonium chrysogenum*, respectively.

As a result of classical strain improvement techniques, the production levels of the antibiotics in *P. chrysogenum* and *A. chrysogenum* have increased dramatically over the past decades. With the increasing knowledge of the biosynthetic pathways leading to penicillins and cephalosporins, and the advent of recombinant DNA technology, new tools for the improvement of production strains and for the in vivo derivatisation of the compounds have become available.

Most enzymes involved in β-lactam biosynthesis have been identified and their corresponding genes been cloned, as can be found in Ingolia and Queener, Med. Res. Rev. 9 (1989), 245–264 (biosynthesis route and enzymes), and Aharonowitz, Cohen, and Martin, Ann. Rev. Microbiol. 46 (1992), 461–495 (gene cloning).

The first two steps in the biosynthesis of penicillin in *P. chrysogenum* are the condensation of the three amino acids L-5-amino-5-carboxypentanoic acid (L-α-aminoadipic acid) (A), L-cysteine (C) and L-valine (V) into the tripeptide LLD-ACV, followed by cyclisation of this tripeptide to form isopenicillin N. This compound contains the typical β-lactam structure.

The third step involves the exchange of the hydrophilic side chain of L-5-amino-5-carboxypentanoic acid by a hydrophobic side chain by the action of the enzyme acyltransferase. The enzymatic exchange reaction mediated by acyltransferase takes place inside a cellular organelle, the microbody, as has been described in EP-A-0 448 180.

Cephalosporins are much more expensive than penicillins. One reason is that some cephalosporins (e.g. cephalexin) are made from penicillins by a number of chemical conversions. Another reason is that, so far, only cephalosporins with a D-5-amino-5-carboxypentanoyl side chain could be subjected to fermentative conversion. Cephalosporin C, by far the most important starting material in this respect, is very soluble in water at any pH, thus implying lengthy and costly isolation processes using cumbersome and expensive column technology. Cephalosporin C obtained in this way has to be converted into therapeutically used cephalosporins by a number of chemical and enzymatic conversions.

The methods current favoured in industry to prepare the intermediate 7-ADCA involve complex chemical steps leading to the expansion and derivatisation of penicillin G. One of the necessary chemical steps to produce 7-ADCA involves the expansion of the 5-membered penicillin ring structure to a 6-membered cephalosporin ring structure (see for instance U.S. Pat. No. 4,003,894). This complex chemical processing is both expensive and noxious to the environment.

Consequently, there is a great desire to replace such chemical processes with enzymatic reactions such as enzymatic catalysis, preferably in an in vivo process. A key to the replacement of the chemical expansion process by enzymatic and in vivo processes is the central enzyme in the cephalosporin biosynthetic pathway, desacetoxycephalosporin C synthetase (DAOCS), also called "expandase".

The expandase enzyme from the bacterium *Streptomyces clavuligerus* was found to carry out, in some cases, penicillin ring expansions. When introduced into *P. chrysogenum*, it can convert the penicillin ring structure into the cephalosporin ring structure in vivo, as described in Cantwell et al., Proc. R. Soc. Lond. B. 248 (1992), 283–289. The expandase enzyme has been well characterised (EP-A-0 366 354) both biochemically and functionally, as has its corresponding gene, cefE. Both physical maps of the cefE gene (EP-A-0 341 892). DNA sequence and transformation studies in *P. chrysogenum* with cefE have been described.

Another source for a ring expansion enzyme is for example the bacterium *Nocardia lactamdurans* (formerly *Streptomyces lactamdurans*) and the fungus *Acremonium chrysogenum* (formerly *Cephalosporium acremonium*). The expandase from *Cephalosporium* is a bifunctional enzyme, having expandase (ring-expansion) as well as 3-hydroxylating activity. Both the biochemical properties of the enzyme and the DNA sequence of the gene have been described (Cortés et al., J. Gen. Microbiol. 133 (1987), 3165–3174; and Coque et al., Mol. Gen. Genet. 236 (1993), 453–458, respectively).

Since the expandase catalyses the expansion of the 5-membered thiazolidine ring of penicillin N to the 6-membered dihydrothiazine ring of DAOC this enzyme would be a logical candidate to replace the ring expansion steps of the chemical process. Unfortunately, the enzyme works on the penicillin N intermediate of the cephalosporin biosynthetic pathway, but not, or relatively inefficiently, on the readily available inexpensive penicillins as produced by *P. chrysogenum*, like penicillin V or penicillin G. Penicillin N is commercially not available and even when expanded, its D-5-amino-5-carboxypentanoyl side chain cannot be easily removed by penicillin acylases.

It has recently been found that the expandase enzyme is capable of expanding penicillins with non-naturally occurring side chains to the corresponding 7-ADCA derivatives. These side chains include adipate (5-carboxyl-pentanoic acid) and various other compounds. This feature of the expandase has been exploited in a process for the in vivo production of adipoyl-7-ADCA in *Penicillium chrysogenum* as disclosed in EP-A-0 532 341. *Penicillium chrysogenum* strains are transformed with the *Streptomyces clavuligerus* expandase to produce adipoyl-6-aminopenicillanic acid (adipoyl-6-APA) when these transformants are fed adipic acid. Subsequently, adipoyl-6-APA is "expanded" to adipoyl-7-ADCA. Production of various other 7-acylated cephalosporins have been disclosed in WO 95/04148 and WO 95/04149. In WO 95/04148 and WO 95/04149 it has been disclosed that addition of 3'-carboxymethyl thiopropionic acid and 3,3'-thiodipropionic acid to the medium yield penicillins that are substrates for the expandase, leading to the synthesis of 2-(carboxyethylthio)acetyl-7-ADCA and 3-(carboxymethylthio)propionyl-7-ADCA, respectively.

Even though expandase displays an activity on penicillins with different side-chains, the expansion of these novel penicillins occurs less efficient as compared to the expansion of the natural substrate, penicillin N. The notion has been the basis for modifying the expandase, aiming to alter the activity on adipoyl-penicillanic acid. Application of mutagenised expandase has been disclosed in WO 98/02551.

The final step in the synthesis of penicillins, the exchange of the α-amino adipoyl side chain of IPN by an alternative side-chain, occurs in the microbody, where the acyltransferase is localised. For optimal expansion of the penicillin, the preferred localisation of expandase is therefore believed to be in the microbody. This is based not only on the fact that the substrate for expandase is believed to be produced in the microbody, but also on the expectation that in the microbody, expandase should be better protected from degradation by proteases, which is a known drawback from the use of *P. chrysogenum* for the production of enzymes (see for example, Theilgaard et al., 1997; Purification and characterisation of δ-(L-α-aminoadipyl)-L-cysteinyl-D-valine synthetase from *Penicillium chrysogenum;* Biochem. J. 327, 185–191).

Modification of cellular localisation of enzymes involved in beta-lactam antibiotic production has been suggested in EP 0 448 180. For example on page 7, penultimate paragraph, it is suggested to localise epimerase and preferably subsequent cephalosporin biosynthetic enzymes like expandase/hydroxylase from *Acremonium chrysogenum* or expandase from *Streptomyces* spec. in the microbodies, to improve the efficiency of the production of cephalosporin or intermediates in *Penicillium chrysogenum.* It was also shown therein, that removal of the microbody targeting signal of acyltransferase, an enzyme involved in the removal of the side chain of acyl-6-APA destroys penicillin production altogether. This strongly suggests, that enzymes involved in beta-lactam production should be localised in the microbodies, if not for reasons of substrate localisation then at least for reasons of stability.

DESCRIPTION OF THE INVENTION

The invention provides DNA, heterologous host cells capable of transcribing, translating or expressing said DNA and methods employing such host cells and cultures thereof for an improved in vivo production of acylated-cephalosporins with higher yield. According to the invention, a host cell is provided comprising an enzyme having expandase activity which is predominantly localised in the cytosol (as opposed to localised mainly in or with the perixisomes or microbodies) of the host cell.

In a preferred embodiment, the invention provides an isolated DNA fragment coding for a modified expandase, which expandase, after expression of said DNA fragment in a *Penicillium chrysogenum* host, is found predominantly in the cytosol of said *Penicillium* host. Such a DNA fragment coding for a modified expandase can for example be obtained by modifying DNA encoding an expandase as found with *Nocardia lactamdurans* (formerly *Streptomyces lactamdurans*) and the fungus *Acremonium chrysogenum,* and other related (i.e. cephalosporin/cephamycin producing) micro-organisms.

The invention provides an isolated DNA fragment encoding a modified expandase that preferably localises predominantly in the cytosol instead of in the microbody of the heterologous host. In a preferred embodiment of the invention such a DNA fragment is obtainable from *Streptomyces clavuligenrus* DNA encoding an expandase, and modified to obtain an DNA fragment encoding an expandase that, when expressed in a *Penicillium chrysogenum* host, is found predominantly in the cytosol of said *Penicillium* host.

Such a modification comprises cloning by recombinant techniques of a nucleotide sequence encoding said expandase, but preferably comprises modifying by recombinant techniques of a sequence coding for a microbody or peroxisome targeting signal in said expandase. Modification can comprise a single or multiple mutation (such as a deletion, insertion, or reversion) of a nucleic acid sequence encoding an expandase, preferably of a sequence encoding a carboxy-terminal amino acid sequence of said expandase.

Amongst the eukaryotic organisms, targeting of proteins to peroxisomes or microbodies has been relatively well studied in non-filamentous yeast. In these organisms, proteins destined for the peroxisome or microbody generally contain a C-terminal targeting sequence, the amino acid sequence of which is generally S (serine) K (lysine) L (leucine), or more generally (Ser/Cys/Ala)-(Lys/His/Arg)-(Leu/Ala). Such a targeting sequence, at least in a homologous context, provides the necessary signal for a protein such as an enzyme to be routed to the microbody, where it finds its final localisation.

For filamentous fungi, such as for *Penicillium chrysogenum,* targeting of proteins to peroxisomes or microbodies has been relatively little studied, and only very little is known about targeting of proteins in a heterologous context, when an organism such as a yeast or fungus is used as a host cell to translate or even express an heterologous protein. This is especially the case when a heterologous protein is derived from a prokaryotic organism such as a bacterium, since bacteria do not have organelles like peroxisomes or microbodies, and thus do not utilise the perixosomal targeting signal in a homologous context. It is generally believed, that, in order for a heterologously expressed protein or enzyme to function well in its host, the respective targeting signals should at least resemble those used by the host in order to find comparative subcellular localisation.

Expandase from the bacterium *S. clavuligerus* generally comprises a C-terminal sequence, SKA (Serine-Lysine-Alanine), that seemingly functions as a peroxisomal targeting sequence when said protein is expressed in a heterologous context in a eukaryotic host. For example, *Penicillium chrysogenum* strains transformed with the *S. clavuligerus* expandase (as for example discussed in EP 0532 341 A1) show localisation of the respective expandase within the peroxisome.

It has been found, that the wild-type expandase from *Streptomyces clavuligerus,* when produced recombinantly in *Penicillium chrysogenum,* predominantly accumulates in the microbodies. Said sequence of three amino acids, Ser-Lys-Ala, apparently serves as a microbody targeting signal in *Pencillium chrysogenum,* although it is somewhat divergent from the consensus sequences for microbody targeting signals in yeast.

When peroxisomal targeting signals, as well as signals that should prevent localisation within peroxisomes, were engineered onto the carboxy terminus of the *S. clavuligerus* expandase, or for that matter onto the carboxy terminus of *Cephalosporium acremonium* expandase/hydrolase, this tendency to localise within the peroxisome did not alter, regardless of the different carboxy terminal amino acid sequences that were added (Verburg et al., P. 35, page 108. In: $7^{th}$ Int. Symp. Gen. Industr. Microorg. 26 Jun.–1 July 1994, Montreal Canada).

Apparently, the enzyme carries an effective targeting signal, causing it to localise, at least predominantly, within the microbody of the heterologous *Penicillium chrysogenum* host cell. However, in one embodiment of the invention, the invention now provides an effective modification of an expandase, altering the tendency to localise within the microbody and leading to a predominant localisation of said expandase in the cytosol of a host.

The tendency to localise at the microbody or peroxisome is governed by N-terminal or C-terminal peroxisome targeting signals (PTSs), modification of said PTS (be it N-terminally or C-terminally) substantially preventing such localisation in the microbodies. An example of such a modification is a modification in a nucleotide sequence coding for a carboxy terminal tripeptide X1—X2—X3, for instance wherein X1 is one amino acid residue selected from the group consisting of Serine, Cysteine and Alanine, X2 is one amino acid residue selected from the group consisting of Lysine, Histidine and Arginine and X3 is Leucine or Alanine. Such tripeptide sequences are also called SKL-like peptides, and the essential sequence of the signal may be a small amino acid at the first, a basic residue at the penultimate and a large non-polar residue at the C-terminal position. The invention provides a DNA fragment encoding an expandase wherein said fragment encoding an SKL-like tripeptide has been modified or selected so as to substantially prevent the expandase to be localised in the microbodies and hence to cause the expandase to be localised predominantly in the cytosol of the host cell upon expression in said heterologous cell.

In a preferred embodiment of the invention, said DNA fragment is obtained from DNA encoding *S. clavuligerus* expandase initially comprising a nucleotide sequence coding for a carboxy-terminal tripeptide Serine-Lysine-Alanine which is modified so as to cause the expandase to be localised predominantly in the cytosol of the host cell upon expression therein. Such a modification is particularly exemplified by a DNA fragment of the invention wherein a nucleotide sequence coding for Serine-Lysine-Alanine has been modified into a sequence coding for Serine-Lysine-Aspartic acid, or where the amino acid at the ultimate position has been deleted or replaced by for example another non-hydrophobic residue.

Yet another modification comprises Serine-Serine-Aspartic acid, or where the amino acid at the penultimate position has been deleted or replaced by a non-positively charged residue.

Yet other modifications comprise deletions of modifications in the first position of the tripeptide that alter the routing of a thus modified protein in a heterologous host and cause it to be predominantly localised in the cytosol of the host cell used.

Yet other modifications comprise deletions or modifications of any of a combination of these three amino acids or codons encoding these carboxy terminal amino acids.

On the one hand, it has surprisingly been found that deliberate modification, using conventional recombinant DNA techniques, of the tripeptidic sequence SKA (or functional variants thereof as explained above) which apparently functions as a microbody targeting signal, causes the heterologously expressed enzyme to accumulate predominantly in the cytosol of the host cell, rather than in the microbodies.

However, on the other hand, variations of proteins in nature are abound, and it is now possible to find microorganisms that comprise an enzyme such as an expandase, that, when said enzyme would be expressed in a heterologous host, would be predominantly localised in the cytosol of said host. Especially proteins or enzymes that have a C-terminal sequence deviant from the above identified targeting sequence are likely candidates to be tested for cytosolic localisation and selected for further use in improving yields of cephalosporin production. In a particular embodiment, the invention provides a nucleotide sequence coding for an expandase which upon expression in a *Pencillium chrysogenum* host cell is localised predominantly in the cytosol, thereby improving cephalosporin yield over those of a host cell expressing a comparable enzyme within or at the microbodies.

Quite contrary to expectation, an enzyme as provided by the invention appears to be stable outside the microbodies. An expandase, as provided by the invention, is still capable of expanding penicillins, even those with non-naturally occurring side chains (see for example EP 97201196.9 and EP 97201197.7) to the corresponding 7-ADCA derivatives.

The invention also provides an isolated DNA fragment encoding a modified or selected enzyme as provided by the invention, said fragment further comprising regulatory regions for expression of said DNA in a eukaryotic host cell. It is for example within the skill of the artisan to provide a DNA fragment with regulatory regions functional in one or more host cells of various organisms, such as animal or plant or a yeast or fungus, origin. In a preferred embodiment, the invention provides a DNA fragment encoding a modified enzyme as provided by the invention comprising regulatory regions suitable for regulating expression in a host cell derived from a micro-organism such as a yeast or fungus.

Surprisingly, it has been found that in a host cell (e.g. *Penicillium chrysogenum*) transformed with a expandase accumulating mainly in the cytosol as opposed to with in the microbodies the production of cephalosporin antibiotics (e.g. adipyl-7-ADCA), is increased, rather than decreased. This is even true when compared to a host cell which has been transformed with DNA coding for an in all other aspects comparable but microbody-localised expandase.

The invention also provides a host cell or host organism (or progeny thereof) having been provided with am modified or selected recombinant DNA fragment encoding a cytosol-localised enzyme as provided by the invention. Such a host organism is for example incorporating, for example as result of transformation of said host organism or ancestor of said host organism, a DNA fragment, optionally comprising regulatory regions or sequences, comprising a nucleotide sequence encoding a modified enzyme as provided by the invention. Such a host is preferably selected from the group consisting of plants and micro-organisms, preferably being a fungus selected from the group consisting of *Penicillium chrysogenum, Aspergillus nidulans* or *A. niger* and *Cephalosporium acremonium*.

The invention also provides cultures of hosts cells or host organisms as provided by the invention. Such a culture comprises cells wherein a functional expandase capable of expanding penicillins with (non-naturally occurring) side chains to the corresponding 7-ADCA derivatives is predominantly found in the cytosol. In a preferred embodiment, the invention provides a culture for large scale fermentation wherein a modified expandase localised in the cytosol contributes to higher production levels of adipoyl-7-ADCA than in a comparable scale fermentation culture utilising wild-type expandase of comparable origin.

In yet another embodiment, the invention provides a host cell, and cultures thereof, having been provided by recombinant techniques with an expandase selected among others for its capacity or tendency to predominantly localise in the cytosol of a heterologous host, be it whether said expandase localises in a homologous context in a microbody or not. Such a host cell can be selected by providing a host cell with a DNA fragment encoding an expandase, and testing whether said expandase localises predominantly in the cytosol. In a preferred embodiment, testing for localisation of said enzyme is performed by electron microscopy, as explained in the experimental part of the description.

The invention also provides a method for making a host cell or organism provided with a modified or selected DNA fragment encoding a modified or selected enzyme as provided by the invention comprising contacting cells under transforming conditions with a DNA fragment as provided by the invention and selecting for cells having obtained said DNA. Transformation of host cells, for example of *P. chrysogenum* or other fungi can, in general, be achieved by different means of DNA delivery, like PEG-Ca mediated protoplast uptake, electroporation or particle gun techniques, and selection of transformants. See for example Van den Hondel en Punt, Gene and Transfer and Vector Development for Filamentous Fungi, in: Applied Molecular Genetics of Fungi (Peberdy, Laten, Ogden, Bennett, eds.), Cambridge University Press (1991). The application of dominant and non-dominant selection markers has been described (Van den Hondel, supra). Selection markers of both homologous (*P. chrysogenum* derived) and heterologous (non-*P. chrysogenum* derived) origin have been described (Gouka et al., J. Biotechnol. 20 (1991) 189–200).

The application of the different transformant selection markers, homologous or heterologous, in the presence or absence of vector sequences, physically linked or not to the non-selectable DNA, in the selection of transformants are well known in the art.

The invention also provides a method for expressing a DNA fragment encoding an expandase in a host cell, wherein said DNA fragment codes for an expandase causing the expandase to be produced and localised predominantly in the cytosol. In a preferred embodiment of the invention such a method comprises providing said DNA fragment with a modification in a nucleotide sequence encoding a carboxy-terminal amino acid sequence, preferably a tripeptide sequence such as SKA found with the expandase of *Streptomyces clavulgerus*. Such a method provided by the invention is preferably used with as host a *Penicillium chrysogenum* cell.

The invention also provides a method for expanding the 5-membered ring of a beta-lactam compound to form a six-membered cephem compound, comprising the steps of growing a host capable of producing said beta-lactam compound under conditions conducive thereto and allowing said host to express an heterologous expandase derived by recombinant means ands capable of expanding the 5-membered ring of said beta-lactam compound from a DNA fragment encoding it, so as to form the said 6-membered cephem compound, characterised in that the said expandase is expressed from a DNA fragment which has been modified or selected to code for an expandase that is produced or at least is localised predominantly in the cytosol of the host cell.

In a preferred embodiment the invention provides a method for expanding the 5-membered ring of a beta-lactam compound by a modified expandase wherein said expandase is localised in the cytosol of a host cell due to a modification in the DNA fragment encoding it, whereby a microbody targeting signal has been modified, preferably wherein a targeting signal comprising a tripeptide amino acid sequence such as obtainable from expandase from *Streptomyces clavuligerus* has been modified.

In the experimental part of this description an example of a method as provided by the invention is given wherein said host cell is *Penicillium chrysogenum*.

In a preferred embodiment of the invention a method is provided wherein said beta-lactam compound is selected from the group consisting of phenylacetyl-6-APA, phenoxyacetyl-6-APA, alpha-aminoadipoyl-6-APA, adipoyl-6-APA, glutaryl-6-APA, or from suberyl-6-APA, pimelyl-6-APA, trans-β-hydromuconyl-6-APA or comparable compounds. Furthermore, the invention provides a method of making a cephem compound comprising the steps of expanding the 5-membered (penam) ring of said beta-lactam compound in a process or method according to the invention and recovering the cephem compound so formed. In a preferred embodiment, the invention provides a method a making a cephem compound in a host cell culture for large scale fermentation wherein the expandase that is predominantly localised in the cytosol of said host cell contributes to higher production levels of adipoyl-7-ADCA than a method of making a cephem compound via comparable scale fermentation culture utilising an expandase (in wild-type or modified form) of comparable origin that is predominantly localised in a microbody. The invention is illustrated in more detail in the following 4 Figures.

Experimental Part

Figure 1:
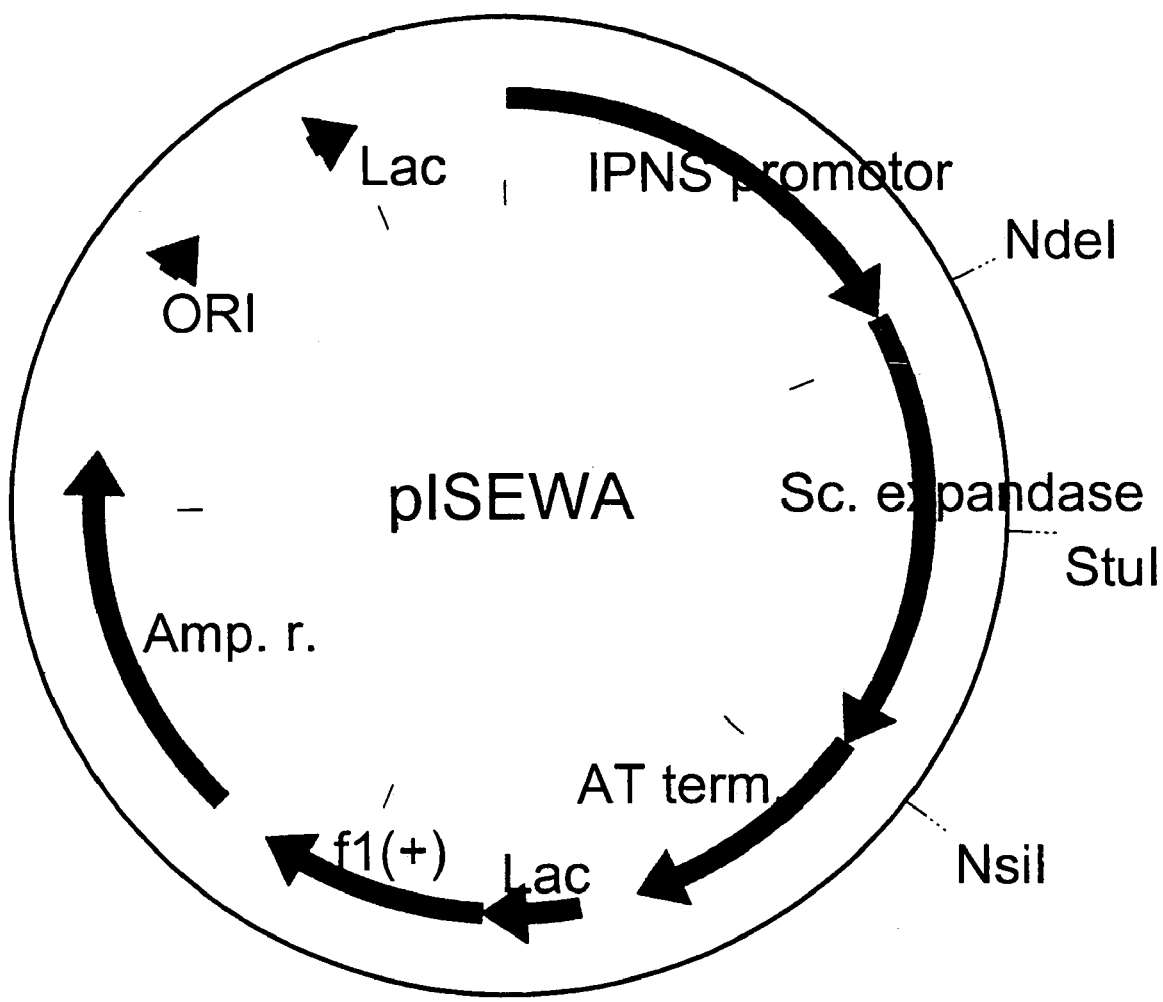
FIG. 1. Schematic representation of plasmid pISEWA.

Transformation of host cells, for example of *P. chrysogenum* or other fungi can, in general, be achieved by different means of DNA delivery, like PEG-Ca mediated protoplast uptake, electroporation or particle gun techniques, and selection of transformants. See for example Van den Hondel en Punt, Gene and Transfer and Vector Development for Filamentous Fungi, in: Applied Molecular Genetics of Fungi (Peberdy, Laten, Ogden, Bennett, eds.), Cambridge University Press (1991). The application of dominant and non-dominant selection markers has been described (Van den Hondel, supra). Selection markers of both homologous (*P. chrysogenum* derived) and heterologous (non-*P. chrysogenum* derived) origin have been described (Gouka et al., J. Biotechnol. 20 (1991) 189–200).

The application of the different transformant selection markers, homologous or heterologous, in the presence or absence of vector sequences, physically linked or not to the non-selectable DNA, in the selection of transformants are well known.

The ring-expansion reaction, mediated by the modified or selected expandase enzyme is introduced into and expressed in this way in *P. chrysogenum*, for instance in strain Wisconsin 54-1255 (deposited at ATCC under accession number 28089). Other strains of *P. chrysogenum,* including mutants of strain Wisconsin 54-1255, having an improved beta-lactam yield, are also suitable.

Furthermore, the modified cefE gene is placed under the transcriptional and translational control of fungal gene control elements. Those elements can be obtained from cloned fungal genes like the *P. chrysogenum* IPNS or pcbC gene, the b-tubulin gene, the *Aspergillus nidulans* gpdA gene, or the *Aspergillus niger* glcA gene.

In accordance with the present invention the β-lactam intermediate adipoyl-7-ADCA is produced in *P. chrysogenum* transformants expressing expandase by adding adipic acid or a salt or an ester thereof to the medium. Suitable salts are for instance those of sodium or potassium, Adipoyl-7-ADCA is efficiently recovered from the medium through a simple solvent extraction, for instance, as follows:

The broth is filtered and an organic solvent immisible with water is added to the filtrate. The pH is adjusted in order to extract the cephalosporin from the aqueous layer. The pH range has to be lower than 4.5; preferably between 4 and 1, more preferably between 2 and 1. In this way the cephalosporin is separated from many other impurities present in the fermentation broth. Preferably a small volume of organic solvent is used, giving a more concentrated solution of the cephalosporin, so achieving reduction of the volumetric flow rates. A second possibility is whole broth extraction at a pH of 4 or lower. Preferably the broth is extracted between 4 and 1 with an organic solvent immiscible with water.

Any solvent that does not interfere with the cephalosporin molecule can be used. Suitable solvents are, for instance, butyl acetate, ethyl acetate, methyl isobutyl ketone, alcohols like butanol etc. Preferably 1-butanol or isobutanol are used.

Hereafter the cephalosporin is back extracted with water at a pH between 4 and 10, preferably between 6 and 9. Again the final volume can be reduced. The recovery can be carried out at temperatures between 0 and 50° C., and preferably at ambient temperatures.

The aqueous cephalosporin solution thus obtained is treated with a suitable enzyme in order to remove the adipoyl side chain and obtain the desired 7-ADCA.

Preferably, an immobilised enzyme is used, in order to be able to use the enzyme repeatedly. The methodology for the preparation of such particles and the immobilisation of the enzymes have been described extensively in EP-A-0222462. The pH of the aqueous solution has a value of, for example pH 4 to pH 9, at which the degradation reaction of cephalosporin is minimised and the desired conversion with the enzyme is optimised. Thus, the enzyme is added to the aqueous cephalosporin solution while maintaining the pH at the appropriate level by, for instance, adding an inorganic base, such as a potassium hydroxide solution, or applying a cation exchange resin. When the reaction is completed the immobilised enzyme is removed by filtration. Another possibility is the application of the immobilised enzyme in a fixed or fluidised bed column, or using the enzyme in solution and removing the products by membrane filtration. Subsequently, the reaction mixture is acidified in the presence of an organic solvent immisicible with water.

Suitable enzymes are, for instance, derived from a *Pseudomonas* SY77 micro-organism having a mutation in one or more of the positions 62, 177, 178 and 179. Also enzymes from other *Pseudomonas* micro-organisms, preferably *Pseudomonas* SE83, optionally having a mutation in one or more of the positions corresponding to the 62, 177, 178 and 179 positions in *Pseudomonas* SY77, may be used.

After adjusting the pH to about 0.1 to 1.5, the layers are separated and the pH of the aqueous layer is adjusted between 2 and 5, more preferably between 3 and 4. The crystalline 7-ADCA is then filtered off.

The deacylation can also be carried out chemically as known in the art, for instance, via the formation of an iminochloride side chain, by adding phosphorus pentachloride at a temperature of lower than 10 aC and subsequently isobutanol at ambient temperatures or lower.

The following examples are offered by way of illustration and not by way of limitation. The overall approach entails i) identification of residues of expandase involved in targeting specificity, ii) selection of expandase proteins or construction of mutant expandase proteins, iii) subcloning of mutant or selected expandase genes in *P. chrysogenum* expression vectors and expression of the expandase in *P. chrysogenum,* iv) determination of the adipoyl-7-ADCA production versus production of α-D-aminoadipoyl-7-ADCA and adipoyl-6-APA.

In a similar way as has been described for the adipoyl side chain a person skilled in the art may also use the modified expandase enzyme in processes disclosed in WO 95/04148 and WO 95/04149 which use 3'-carboxymethylthiopropionic acid and 3,3'-thiodipropionic acid as side chains, yielding 2-(carboxyethylthio)acetyl-7-ADCA and a mixture of 3-(carboxymethylthio)propionyl-7-ADCA and 2-(carboxyethylthio)acetyl-7-ADCA respectively.

Example 1

Site-directed Mutagenesis of the *S. clavuligerus* cefE Gene

Figure 2:
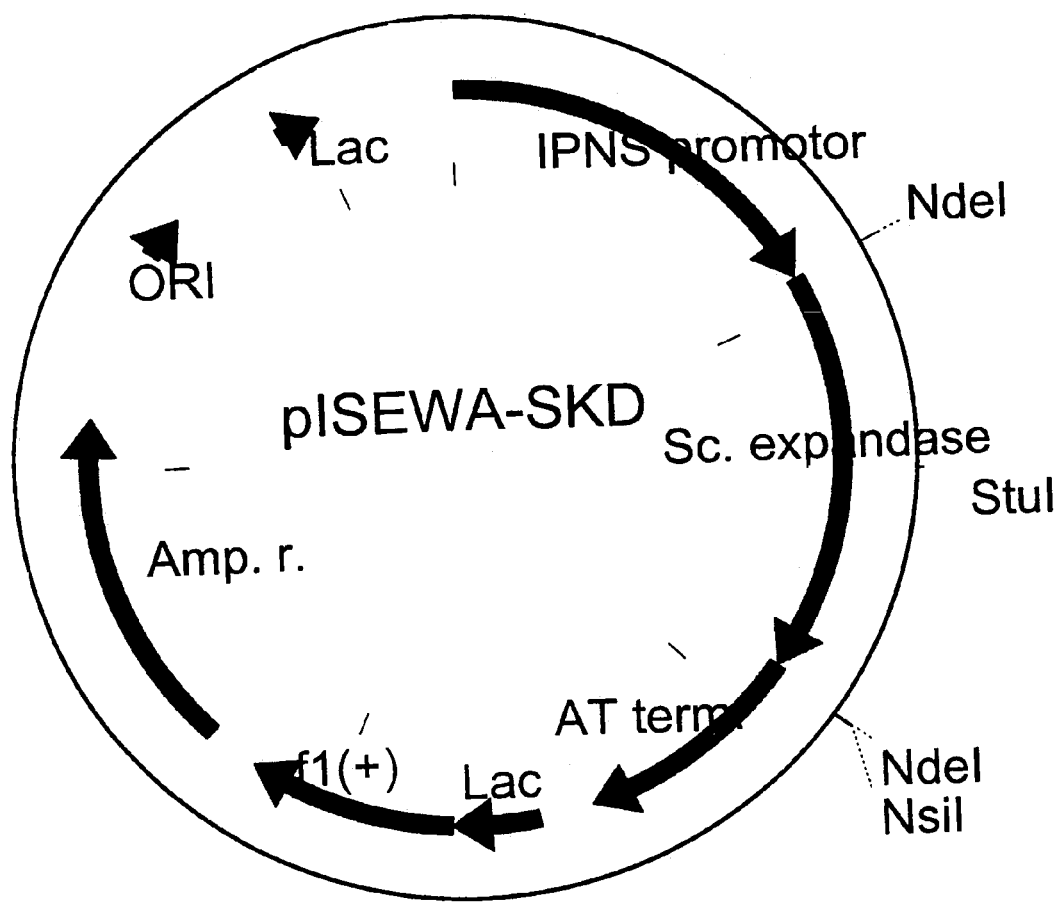
FIG. 2. Schematic representation of plasmid ISEWA-SKD.

Techniques involved in the genetic manipulation of the expandase gene are well described. Sources that can be used as template in PCR reactions include chromosomal DNA preparations from publicly available *Streptomyces clavuligerun* strains (such as ATCC 27064), or expression cassetes such pZEx (described in PCT/EP 97/03879) and pISEWA (described in EP-02812P). The expandase expression cassette pISEWA (FIG. 1) contains the wild type *Streptomyces clavuligerus* expandase gene including the IPNS promoter and AT terminator. In order to disrupt the peroxisomal targeting of expandase, the sequence of the C-terminus of CefE is mutated from SKA to SKD. To that end, with pISEWA as a template, a PCR reaction is performed, using primers 1 and 2 (see table 1). PCR is performed with a proof-reading polymerase. After a denaturation step (2 min 98° C.), part of the cefE gene is amplified in 25 cycli (1.15 min 94° C., 45 sec 55° C., 1 min 72° C.) followed by an extension step (8 min, 72° C.). The product of this reaction runs from the StuI site in cefE (about 450 bp from the start of translation; see Kovacevic et al.: Cloning, characterisation, and expression in *Escherichia coli* of the *Streptomyces clavuligerus* gene encoding desacetoxycephalosporin C synthetase, J. Bacteriol., 171, 754–760, 1989) to an NsiI site downstream from the stop codon. After verification of the sequence by nucleotide sequencing, the StuI-NsiI fragment is used to exchange the 'wild-type' cefE fragment in pISEWA. Thus, plasmid pISEWA-SKD is generated (FIG. 2).

TABLE 1

Primers used in the construction of mutant expandase. The StuI site in primer 1, and the NsiI site in primer 2, are underlined.

| Primer | Sequence (5' -> 3') | |
|---|---|---|
| 1 | G<u>AGGCCT</u>TCCTCGACTGCGAGCCG | SEQ. ID. No.: 1 |
| 2 | CAAAG<u>ATGCAT</u>ATGCTCGTCATGAAGAGCC TACTAGTCCTTGGATGTGCGGCG | SEQ. ID. No.: 2 |

Example 2

Transformation of a *P. chrysogenum* Strain

Techniques involved in the transfer of DNA to protoplasts of *P. chrysogenum* are well known in the art and described in many references, including Finkelstein and Ball (eds.), Biotechnology of filamentous fungi, technology and products, Butterworth-Heinemann (1992); Bennett and Lasure (eds.) More Gene Manipulations in fungi, Academic Press (1991); Turner, in: Pühler (ed), Biotechnology, second completely revised edition, VHC (1992). The Ca-PEG mediated protoplast transformation is used as described in EP 635574. The constructs pISEWA and pISEWA-SKD are thus introduced into *P. chrysogenum* Wisconsin 54-1255 (ATC 28089) by co-transformation with GBGLA28 (EP 635574), which enables *P. chrysogenum* transformants to grow on selection medium containing acetamide as sole nitrogen source. More preferably, a strain is utilised that has a more pronounced capacity to produce penicillins. Examples are strains such as CBS 455.95.

Example 3

Selection: Liquid Cultures

Transformants are purified by repeated cultivation on selective medium. Single stable colonies are used for further screening on the presence of the expandase gene by bioassay. Transformants are grown on agar medium. *E. coli* ESS2231 is used as indicator bacterium in an agar overlay, that also contains Bacto penase to be able to discriminate between penicillin and cephalosporin production according to methods well known in the art and described for example in Guttiérez et al., Mol. Gen. Genet. 225 (1991), 56–64. The presence of the cefE gene in the transformants is confirmed by PCR as described for example in WO 95/04149 on chromosomal DNA, using primers 1 and 2 (Table). Expandase-positive transformants are selected for further screening on the capacity to produce cephalosporins as described for example in WO 95/04149. Transformants are used to inoculate shake flasks with liquid medium as described for example in WO 95/04149. Transformants are inoculated at $2*10^6$ conidia/ml into a seed medium consisting of for example (g/l): glucose, 30: $(NH4)_2SO_4$, 10: $KH_2PO_4$, 10, trace element solution I ($MgSO_4$ 7 $H_2O$, 25; $FeSO_4$ 7 $H_2O$, 10; $CuSO_4$ 5 $H_2O$, 0.5; $ZnSO_4$ 7 $H_2O$, 2; $Na_2SO_4$, 50; $MnSO_4H_2O$, 2; $CaCl_2$ 2 $H_2O$, 5) 10 (ml/l) (pH before sterilisation 6.5).

Figure 3:
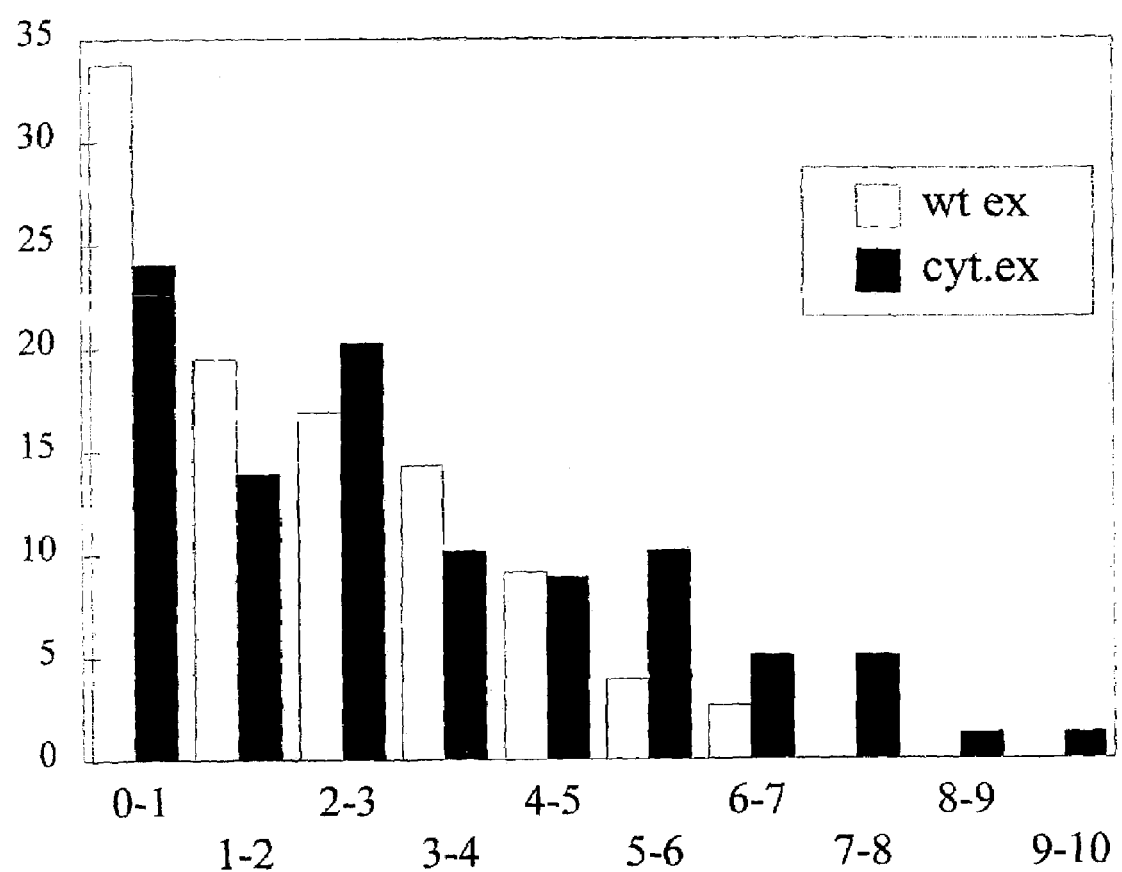
FIG. 3. Adipoyl-7-ADCA productivities of a large number (about 80) of transformants derived from transformations with plasmids pISEWA (open bars) and pISEWA-SKD (solid bars). X-axis: productivity class (arbitrary Units): Y-axis: % of transformants per class.

The seed medium is incubated for 48–72 hours at 25–30° C. and subsequently used to inoculate 10–20 volumes of a production medium containing (g/l) lactose, 80; $CaSO_4$, 4; urea, 3; $MgSO_4$ 7 $H_2O$, 2; $KH_2PO_4$, 7, NaCl, 0.5; $(NH_4)_2SO_4$, 6; $FeSO_4$ 7 $H_2O$, 0.1; adipic acid, 2 to 5; trace element solution II ($CuSO_4$, 5 $H_2O$, 0.5; $ZnSO_4$, 7 $H_2O$, 2; $MnSO_4$ $H_2O$, 2; $Na_2SO_4$, 50), 10 (ml/l) (pH before sterilisation 5.5–6.0). The incubation is then continued for another 96–120 hours. Filtrates of well grown cultures are analysed by HPLC and NMR for production of adipoyl-7-ADCA. As FIG. 3 shows, the transformants with the expandase predominantly localised in the cytosol perform significantly better than transformants with the expandase localised in the microbody.

Example 4

Localisation of Expandase

Figure 4:
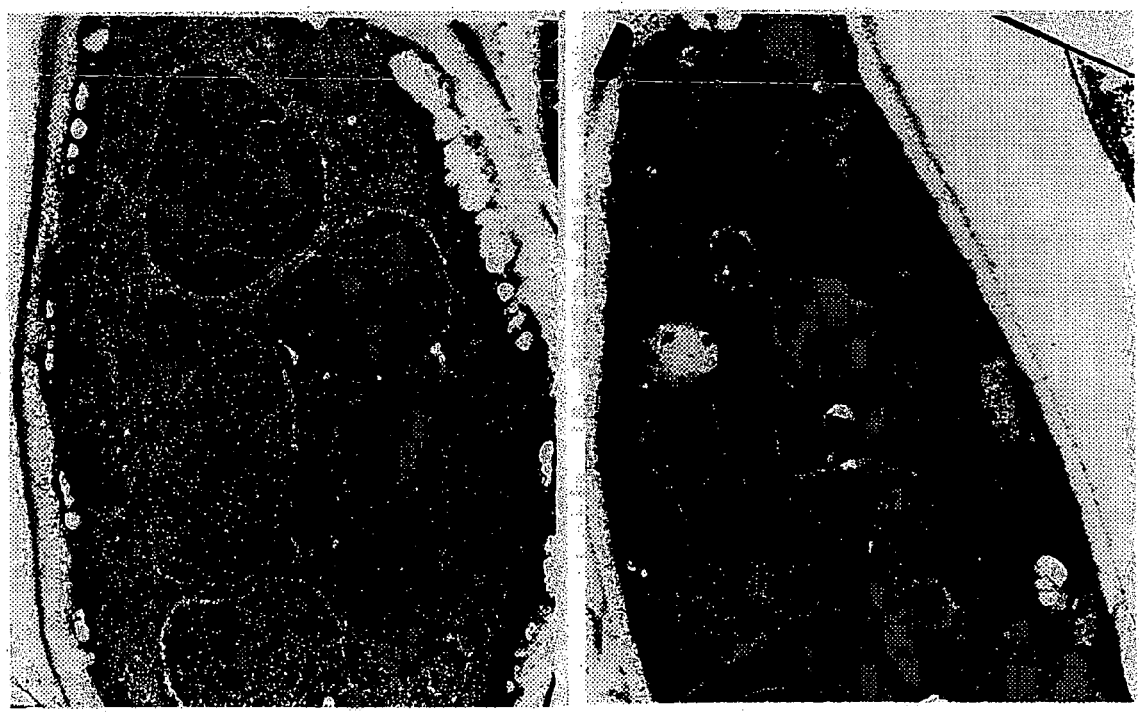
FIG. 4. EM photographs of a transformant expressing wild-type expandase (panel A) and a transformant expressing expandase with a non-targeting signal (SKD-> SKD, panel B). The gold particles indicate the presence of expandase. N: nucleus, M: mitochondrion, P: peroxisome (microbody).

In order to assess that the mutation of the C-terminus of expandase results in a block in the transport of expandase to the peroxisome, electron microscopy is used. Samples are fixed using glutaraldehyde, according to a procedure described by Waterham et al., J. Cell Biol. 127:737–749 (1994). Localisation studies are performed using immunocytochemistry with an anti-expandase polyclonal antibody. FIG. 4 shows expandase accumulating predominantly in the cytosol or in the microbody.

Example 5

Performance of Expandase Mutants on Larger Scales

To determine the performance of transformants with the mutated expandase in larger scale fermentations, from both transformations strains are selected for further analysis. Thus, a mutant expandase transformant is chosen that produces 10% more adipoyl-7-ADCA than the transformant that is selected from the transformation with the wild-type expandase gene. When strains are grown in a 10 L fermenter the amount of adipoyl-7-ADCA in the culture with the expandase localised predominantly in the cytosol is higher than in the fermentation with expandase localised predominantly in the microbody. Thus, expandase predominantly localised in the cytosol is apparently stable enough to maintain stable productivity and improved yield in a long-term or large-scale fermentation.

What is claimed is:

1. A method to provide an altered expandase which will localize in the cytosol of a *Penicillium chrysogenum* host which method comprises altering the consensus C-terminal targeting sequence of said expandase from $X^1$—$X^2$—$X^3$ wherein $X^1$ is ser, cys, or ala;
$X^2$ is lys, his or arg; and
$X^3$ is leu or ala;
so that in the altered expandase $X^2$ is a non-positively charged residue; and/or
$X^3$ is a non-hydrophobic residue.

2. The method of claim 1, wherein in said altered expandase, $X^1$ is ser;
$X^2$ is ser; and
$X^3$ is asp.

3. The method of claim 1, wherein in said altered expandase, $X^1$ is ser;
$X^2$ is lys; and
$X^3$ is asp.

4. An altered expandase, wherein the unaltered form of said expandase is that of *Streptomyces clavuligerus,* having a C-terminal consensus sequence of $X^1$—$X^2$—$X^3$, wherein $X^1$ is ser, $X^2$ is lys, and $X^3$ is ala;

the alteration consisting of altering the C-terminal consensus sequence to:
$X^1$ is ser, cys or ala;
$X^2$ is any amino acid; and
$X^3$ is a non-hydrophobic amino acid;
wherein said altered expandase when expressed in a *Penicillium chrysogenum* host is localized in the cytosol of said host.

5. The altered expandase of claim 4, wherein $X^1$ is ser, $X^2$ is lys; and $X^3$ is asp.

6. The altered expandase of claim 4, wherein $X^1$ is ser; $X^2$ is ser; and $X^3$ is asp.

7. An isolated DNA fragment which encodes an altered expandase, wherein the unaltered form of said expandase is that of *Streptomyces clavuligerus,* having a C-terminal consensus sequence of $X^1$—$X^2$—$X^3$, wherein $X^1$ is ser, $X^2$ is lys, and $X^3$ is ala;

the alteration consisting of altering the C-terminal consensus sequence to:
$X^1$ is ser, cys or ala;
$X^2$ is any amino acid; and
$X^3$ is a non-hydrophobic amino acid;
wherein said altered expandase when expressed in a *Penicillium chrysogenum* host is localized in the cytosol of said host.

8. The DNA fragment of claim 7, which further comprises at least one regulatory region for expression.

9. A host cell which is modified to contain the isolated DNA fragment of claim 8.

10. The recombinant host cell of claim 9, which is a yeast or fungus.

11. The host cell of claim 9, which is *Penicillium chrysogenum, Aspergillus nidulans, Aspergillus niger* and *Acremonium chrysogenum.*

12. A host cell according to claim 11, wherein the host is a strain of *Penicillium chrysogenum.*

13. A method to produce an altered expandase that is localized in the cytosol which method comprises culturing the cell of claim 9 whereby expression of said altered expandase is effected.

14. A method for making a host cell that comprises expandase localized to the cytosol, comprising the steps of contacting cells under transforming conditions for said hosts with the DNA of claim 8.

* * * * *

SEQUENCE LISTING

<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: StuI site primer

<400> SEQUENCE: 1
gaggccttcc tcgactgcga gccg            24

```
<210> SEQ ID NO 2
<211> LENGTH: 53
<212> TYPE: DNA
<213> ORGANISM: Artificial Sequence
<220> FEATURE:
<223> OTHER INFORMATION: Nsil site primer

<400> SEQUENCE: 2
caaagatgca tatgctcgtc atgaagagcc tactagtcct tggatgtgcg gcg         53
```